(12) United States Patent
Kubota et al.

(10) Patent No.: US 9,238,219 B2
(45) Date of Patent: Jan. 19, 2016

(54) ZEOLITE, MANUFACTURING METHOD OF THE SAME, AND CATALYTIC CRACKING BATALYST OF PARAFFIN

(71) Applicants: NIPPON CHEMICAL INDUSTRIAL CO., LTD., Tokyo (JP); NATIONAL UNIVERSITY CORPORATION YOKOHAMA NATIONAL UNIVERSITY, Yokohama-shi, Kanagawa (JP); The University of Tokyo, Tokyo (JP)

(72) Inventors: Yoshihiro Kubota, Yokohama (JP); Satoshi Inagaki, Yokohama (JP); Raita Komatsu, Yokohama (JP); Keiji Itabashi, Tokyo (JP); Tatsuya Okubo, Tokyo (JP); Toyohiko Hieda, Tokyo (JP)

(73) Assignees: UniZeo Co., Ltd., Tokyo (JP); NAT'L UNIVERSITY CORP. YOKOHAMA NAT'L UNIVERSITY, Yokohama-shi, Kanagaya (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 13/813,104

(22) PCT Filed: Nov. 22, 2012

(86) PCT No.: PCT/JP2012/080308
§ 371 (c)(1),
(2) Date: Jan. 29, 2013

(87) PCT Pub. No.: WO2013/077404
PCT Pub. Date: May 30, 2013

(65) Prior Publication Data
US 2014/0322126 A1    Oct. 30, 2014

(30) Foreign Application Priority Data

Nov. 25, 2011 (JP) .................. 2011-258328
Nov. 25, 2011 (JP) .................. 2011-258329
Nov. 22, 2012 (JP) .................. 2012-255811

(51) Int. Cl.
| | |
|---|---|
| *C01B 39/46* | (2006.01) |
| *B01J 29/70* | (2006.01) |
| *C07C 4/06* | (2006.01) |
| *C01B 39/48* | (2006.01) |
| *C01B 39/02* | (2006.01) |
| *B01J 35/00* | (2006.01) |
| *C07B 61/00* | (2006.01) |
| *C07C 11/06* | (2006.01) |
| *C10G 11/00* | (2006.01) |

(52) U.S. Cl.
CPC .............. *B01J 29/7007* (2013.01); *B01J 29/70* (2013.01); *C01B 39/026* (2013.01); *C01B 39/48* (2013.01); *B01J 35/002* (2013.01); *B01J 2229/186* (2013.01); *B01J 2229/36* (2013.01); *B01J 2229/37* (2013.01); *C07B 61/00* (2013.01); *C07C 4/06* (2013.01); *C07C 11/06* (2013.01); *C10G 11/00* (2013.01)

(58) Field of Classification Search
CPC .... C01B 39/026; C01B 39/46; B01J 29/7007; B01J 2229/186; B01J 2229/36; B01J 2229/37
See application file for complete search history.

(56) References Cited

U.S. PATENT DOCUMENTS

| | | | |
|---|---|---|---|
| 3,308,069 A | 3/1967 | Wadlinger et al. | |
| 4,642,226 A * | 2/1987 | Calvert et al. | 423/706 |
| 5,139,759 A * | 8/1992 | Cannan et al. | 423/709 |
| 5,227,558 A * | 7/1993 | Shamshoum et al. | 585/446 |

FOREIGN PATENT DOCUMENTS

| | | |
|---|---|---|
| JP | 2010-215434 A | 9/2010 |
| WO | 2011/013560 A1 | 2/2011 |
| WO | 2012/137132 A1 | 10/2012 |

OTHER PUBLICATIONS

Majano et al, "Al-Rich zeolite Beta by Seeding in the Absence of Organic Template", Chem. Mater. (2009), 21, 4184-4191.*
Kunkeler et al, "Zeolite Beta: The Relationship between Calcination Procedure, Aluminum Configuration, and Lewis Acidity", Journal of Catalysis 180 (1998) pp. 234-244.*
Renzini, M.S. et al., "Stability of ZSM-11 and Beta zeolites during the catalytic cracking of low-density polyethylene", Journal of Analytical and Applied Pyrolysis, Elsevier BV, NL, vol. 92, No. 2, Aug. 19, 2011, pp. 450-455, Cited in Extended European Search Report dated Nov. 17, 2014.
Corma, A. et al., "Isobutane/2-butene alkylation on zeolite beta: Influence of post-synthesis treatments", Applied Catalysis A: General, Elsevier Science, Amsterdam, NL, vol. 142, No. 1, Aug. 1, 1996, pp. 139-150, Cited in Extended European Search Report dated Nov. 17, 2014.

(Continued)

*Primary Examiner* — David M Brunsman
(74) *Attorney, Agent, or Firm* — Westerman, Hattori, Daniels & Adrian, LLP

(57) ABSTRACT

Provided is a beta-type zeolite which has a high catalytic activity and is not easily deactivated. The beta-type zeolite of the invention has a substantially octahedral shape, has a Si/Al ratio of 5 or more, and is a proton-type zeolite. The Si/Al ratio is preferably 40 or more. This beta-type zeolite is preferably obtained by transforming a raw material beta-type zeolite synthesized without using a structure directing agent into an ammonium-type zeolite through ion exchange, then, exposing the beta-type zeolite to water vapor, and subjecting the exposed beta-type zeolite to an acid treatment.

8 Claims, 12 Drawing Sheets

(56) References Cited

OTHER PUBLICATIONS

Pinheiro, A. N. et al., "Highly stable dealuminated zeolite support for the production of hydrogen by dry reforming of methane", Applied Catalysis A: General, Elsevier Science, Amsterdam, NL, vol. 355, No. 1-2, Feb. 28, 2009, pp. 156-168, Cited in Extended European Search Report dated Nov. 17, 2014.

Marques, J. P. et al., "Dealumination of HBEA zeolite by steaming and acid leaching: distribution of the various aluminic sprecies and identification of the hydroxyl groups", Comptes Rendus—Chimie, Elsevier, Paris, FR, vol. 8, No. 3-4, Mar. 1, 2005, pp. 399-410, Cited in Extended European Search Report dated Nov. 17, 2014.

Extended European Search Report dated Nov. 17, 2014, issued in corresponding European Patent Application No. 12851632.5 (7 pages).

Inagaki et al. "Selective formation of propylene by hexane cracking over MCM-68 zeolite catalyst", Chemical Communications, (Feb. 23, 2010,)vol. 46, No. 15, pp. 2662-2264, cited in Extended European Search Report dated Apr. 22, 2015.

Inagaki et al., "Supplementary Information—Selective formation of propylene by hexane cracking over MCM-68 zeolite catalyst Electronic", Chemical Communications, (Feb. 23, 2010), pp. 1-5, cited in Extended European Search Report dated Apr. 22, 2015.

Shibata et al., "Synthetic investigation on MCM-68 zeolite with MSE topology and its application for shape-selective alkylation of biphenyl", Microporous and Mesoporous Materials, Elsevier Science, Publishing, New York, US, (Dec. 1, 2008,)vol. 116, No. 1-3, pp. 216-226, cited in Extended European Search Report dated Apr. 22, 2015.

Triantafillidis et al. "Effect of the degree and type of the dealumination method on the structural, compositional and acidic characteristics of H-ZSM-5 zeolites", Microporous and Mesoporous Materials, Elsevier Science, Publishing, New York, US, (Oct. 1, 2001,)vol. 47, No. 2-3, pp. 369-388, cited in Extended European Search Report dated Apr. 22, 2015.

Extended European Search Report dated (Apr. 22, 2015,)issued in counterpart Patent Application No. 12851632.5 (16 pages).

\* cited by examiner (a) BETA-TYPE ZEOLITE MANUFACTURED WITHOUT USING OSDA (b) BETA-TYPE ZEOLITE AFTER DEALUMINATING (a) EXAMPLE 1

(a) BETA-TYPE ZEOLITE MANUFACTURED USING OSDA (b) BETA-TYPE ZEOLITE AFTER DEALUMINATING (a)
COMPARATIVE EXAMPLE 3

ZEOLITE, MANUFACTURING METHOD OF THE SAME, AND CATALYTIC CRACKING BATALYST OF PARAFFIN

This application is a 371 filing of PCT/JP2012/080308, filed Nov. 22, 2012.

TECHNICAL FIELD

The present invention relates to a beta-type zeolite and a MSE-type zeolite. The beta-type zeolite and the MSE-type zeolite of the invention are promising substances as a solid acid catalyst or an adsorbent, and, in more detail, are particularly promising as a catalytic cracking catalyst of paraffin, for example, a cracking catalyst of a long-chain hydrocarbon in the petrochemical industry. Also, the beta-type zeolite and the MSE-type zeolite are promising substances as a hydrocarbon trap for purifying the exhaust gas from an internal-combustion engine. In addition, the invention relates to a manufacturing method of a beta-type zeolite and a MSE-type zeolite having an increased Si/Al ratio from a beta-type zeolite and a MSE-type zeolite as raw materials.

BACKGROUND ART

The beta-type zeolite is a useful substance as a solid acid catalyst or an adsorbent, and, currently, a large amount of the beta-type zeolite is globally used as a catalyst in the petrochemical industry or a hydrocarbon trap for purifying the exhaust gas of an internal-combustion engine. A variety of synthesizing methods of a beta-type zeolite have been proposed. An ordinary method is a method in which a compound including tetraethylammonium ions is used as a structure directing agent (hereinafter abbreviated to "organic SDA"). Such a method is described in, for example, Patent Citation 1 below. However, although the compound including tetraethylammonium ions is expensive, most of the excessive portion is decomposed after completion of the crystallization of a beta-type zeolite, and decomposition is the only method that can remove the portion incorporated into crystals, and therefore it is not possible to collect and recycle the compound. Therefore, a beta-type zeolite manufactured using the above method is expensive. Furthermore, since tetraethylammonium ions are incorporated into crystals, it is necessary to remove tetraethylammonium ions through firing when a beta-type zeolite is used as an adsorbent or a catalyst. The exhaust gas at this time causes environmental contamination, and a large amount of a chemical is required for a detoxifying treatment of a synthesis mother liquid. As such, since the synthesizing method of a beta-type zeolite using tetraethylammonium ions is a manufacturing method which is not only expensive, but also causes a large environmental load, there has been a demand for realization of a manufacturing method in which the organic SDA is not used.

Under the above circumstance, in recent years, a synthesizing method of a beta-type zeolite in which the organic SDA is not used has been proposed in Patent Citation 2. In the document, a silica source, an alumina source, an alkali source and water are mixed so as to form a reaction mixture having a specific composition; a beta-type zeolite not including an organic compound which has a $SiO_2/Al_2O_3$ ratio of 8 to 30 and an average particle diameter of 150 nm or more is used as a seed crystal, the beta-type zeolite is added to the reaction mixture at a proportion of 0.1 mass % to 20 mass % with respect to the silica component in the reaction mixture; and the reaction mixture to which the seed crystal is added is enclosure-heated at 100° C. to 200° C., thereby synthesizing a beta-type zeolite without using the organic SDA.

However, in a case in which the beta-type zeolite is used as a catalyst in the petrochemical industry or a hydrocarbon trap for purifying the exhaust gas of an internal-combustion engine, it is advantageous to increase the Si/Al ratio from the viewpoint of performance improvement. A method for increasing the Si/Al ratio in the beta-type zeolite is described in, for example, Patent Citation 3, and a method in which a water vapor treatment and an acid treatment are carried out sequentially is known.

[Patent Citation 1] U.S. Pat. No. 3,308,069
[Patent Citation 2] Pamphlet of the International Publication No. 2011/013560
[Patent Citation 3] Japanese Patent Application Laid-Open No. 2010-215434

DISCLOSURE OF INVENTION

Technical Problem

However, there is a case in which, when only the Si/Al ratio of the beta-type zeolite is increased, the catalytic activity of the beta-type zeolite degrades during use at a high temperature. In addition, there is the same problem in a MSE-type zeolite which is similar to the beta-type zeolite in the structure and various properties, such as catalyst characteristics.

An object of the invention is to provide a zeolite which can solve a variety of the above disadvantages of the related art, and a manufacturing method of the same.

Technical Solution

The invention solves the above problem by providing a beta-type zeolite which has a substantially octahedral shape, has a Si/Al ratio of 5 or more, and is a proton-type zeolite.

In addition, the invention provides a MSE-type zeolite which is obtained by transforming a raw material MSE-type zeolite, which has a Si/Al ratio of 5 or more, is a proton-type, and is synthesized without using a structure directing agent, into an ammonium-type zeolite through ion exchange, then, exposing the MSE-type zeolite to water vapor, and subjecting the exposed beta-type zeolite to an acid treatment.

In addition, the invention provides a catalytic cracking catalyst of paraffin which includes the beta-type zeolite and the MSE-type zeolite.

In addition, the invention provides a manufacturing method of a beta-type zeolite in which a raw material beta-type zeolite is transformed into an ammonium-type zeolite through ion exchange, then, the beta-type zeolite is exposed to water vapor, and the exposed beta-type zeolite is subjected to an acid treatment, thereby obtaining a beta-type zeolite having an increased Si/Al ratio, wherein a beta-type zeolite synthesized without using a structure directing agent is used as the raw material beta-type zeolite to be ion-exchanged.

Furthermore, the invention provides a manufacturing method of a MSE-type zeolite in which a raw material MSE-type zeolite is transformed into an ammonium-type zeolite through ion exchange, then, the MSE-type zeolite is exposed to water vapor, and the exposed MSE-type zeolite is subjected to an acid treatment, thereby obtaining a MSE-type zeolite having an increased Si/Al ratio, wherein a MSE-type zeolite synthesized without using a structure directing agent is used as the raw material MSE-type zeolite to be ion-exchanged.

Advantageous Effects

According to the invention, a beta-type zeolite and a MSE-type zeolite, which have a high catalytic activity and are not easily deactivated, are provided. In addition, according to the invention, it is possible to easily manufacture a beta-type zeolite and a MSE-type zeolite having a high Si/Al ratio without breaking the crystal structure of the zeolites.

BEST MODE FOR CARRYING OUT THE INVENTION

Figure 1:
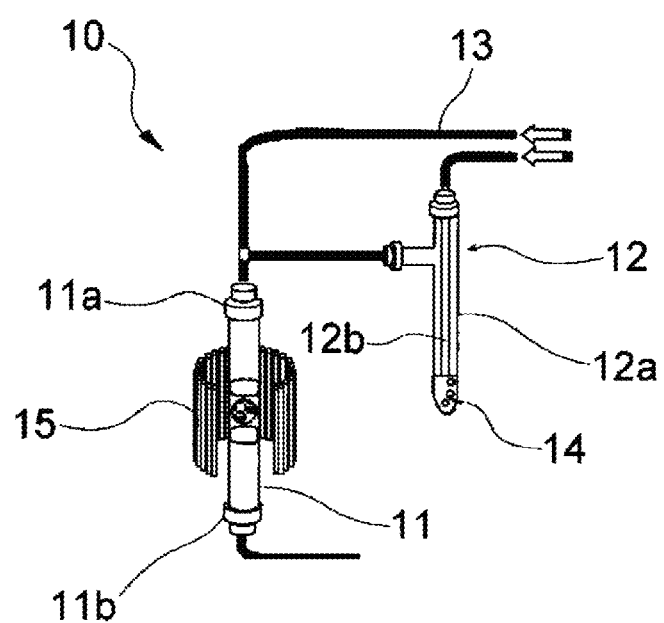
FIG. 1 is a schematic view showing an apparatus used during exposure of a beta-type zeolite to water vapor.

Hereinafter, the invention will be described in detail. In the description below, the "zeolite" indicates either one or both of a "beta-type zeolite" and a "MSE-type zeolite" according to the context. Among the beta-type zeolite and the MSE-type zeolite of the invention, the beta-type zeolite has a substantially octahedral appearance configuration. In the past, there were known beta-type zeolites having a low Si/Al ratio and a substantially octahedral appearance configuration, but there were no known beta-type zeolites having a high Si/Al ratio and a substantially octahedral appearance configuration. The reason is considered to be that, since there are many cases in which the beta-type zeolite having a high Si/Al ratio is obtained using the organic SDA, the beta-type zeolite does not move into a growth mode of a substantially octahedral crystal due to the generation of nuclei induced from the organic SDA.

The beta-type zeolite and the MSE-type zeolite of the invention are high silica zeolites having a Si/Al ratio of 5 or more. Since having the above Si/Al ratio, the beta-type zeolite and the MSE-type zeolite of the invention are useful as a catalyst used at a high temperature, such as a cracking catalyst of a long-chain hydrocarbon (for example, hexane) in the petrochemical industry or a catalyst for purifying the exhaust gas of an internal-combustion engine. There have been known beta-type zeolites and MSE-type zeolites having a Si/Al ratio of 5 or more, but the appearance configurations of the zeolites are irregular, and, particularly, there has not been known a beta-type zeolite having a substantially octahedral shape like the invention. The Si/Al ratios of the beta-type zeolite and the MSE-type zeolite of the invention are preferably higher from the viewpoint of the catalytic activity and the like. Specifically, the Si/Al ratio is preferably 14 or more, more preferably 40 or more, and particularly preferably 55 or more. The upper limit value of the Si/Al ratio is not particularly limited; however, when the upper limit is 200, preferably 190, and particularly 150, a sufficiently satisfactory catalytic activity and the like can be obtained.

As described above, the beta-type zeolite of the invention is characterized by both (i) having an appearance configuration of a substantially octahedral shape and (ii) having a Si/Al ratio of 5 or more. The beta-type zeolite which thus far has been known is equipped with only one of (i) and (ii) as described above, and there has been no beta-type zeolite equipped with both (i) and (ii). In addition, the inventors found that a beta-type zeolite equipped with both (i) and (ii) has a high catalytic activity, and the activity is not easily deactivated even at a high temperature, and completed the invention. Meanwhile, the MSE-type zeolite is characterized by having a Si/Al ratio of 5 or more. A MSE-type zeolite having the above Si/Al ratio has a high catalytic activity, and the activity is not easily deactivated even at a high temperature, similarly to the beta-type zeolite.

The beta-type zeolite and the MSE-type zeolite of the invention advantageously have a Brønsted acid site in order to be used as a variety of catalysts. From the above viewpoint, the zeolites of the invention are proton-type zeolites. However, the zeolites of the invention may include a small amount of ammonium ions or alkali metal ions within a range in which the effects of the invention are not impaired.

The average particle diameters of the beta-type zeolite and the MSE-type zeolite of the invention are preferably 0.2 μm to 2.0 μm, and more preferably 0.5 μm to 1.0 μm. In addition, the BET specific surface area is 400 m$^2$/g to 650 m$^2$/g, preferably 500 m$^2$/g to 650 m$^2$/g, and more preferably 550 m$^2$/g to 650 m$^2$/g. Furthermore, the volume of a micro hole is preferably 0.10 m$^3$/g to 0.28 m$^3$/g, and more preferably 0.15 m$^3$/g to 0.25 m$^3$/g. The specific surface area and the volume are measured by using a BET surface area measuring apparatus.

The beta-type zeolite of the invention preferably has diffraction peaks in at least the locations described in Tables 1 and 2 below in the diffraction pattern obtained through X-ray diffraction in which CuKα1 rays are used. Meanwhile, Table 1 shows the diffraction patterns, and Table 2 shows preferable peak intensity ratios. In Table 1, "vs" indicates an extremely strong relative intensity (80% to 100%), "s" indicates a strong relative intensity (60% to 80%), "m" indicates an intermediate relative intensity (40% to 60%), and "w" indicates a weak relative intensity (0% to 40%). In Table 2, the peak intensity (%) refers to a relative intensity when the peak intensity of the maximum peak in the diffraction pattern is set to 100.

TABLE 1

| Location of peak 2θ (°) | Relative intensity |
|---|---|
| 21.08-21.58 | w |
| 22.12-22.62 | vs |
| 25.00-25.50 | w |
| 26.80-27.30 | w |
| 28.38-28.88 | w |
| 29.26-29.86 | w |
| 30.00-30.70 | w |
| 32.92-33.62 | w |
| 43.00-43.85 | w |

TABLE 2

| Location of peak 2θ (°) | Peak intensity (%) |
|---|---|
| 21.08-21.58 | 10-30 |
| 22.12-22.62 | 100 |
| 25.00-25.50 | 8-28 |
| 26.80-27.30 | 7-27 |
| 28.38-28.88 | 5-25 |
| 29.26-29.86 | 7-37 |
| 30.00-30.70 | 2-17 |
| 32.92-33.62 | 4-19 |
| 43.00-43.85 | 3-18 |

The MSE-type zeolite of the invention preferably has diffraction peaks in at least the locations described in Tables 3 and 4 below in the diffraction pattern obtained through X-ray diffraction in which CuKα1 rays are used. Meanwhile, Table 3 shows the diffraction patterns, and Table 4 shows preferable peak intensity ratios. In Table 3, "vs" indicates an extremely strong relative intensity (80% to 100%), "s" indicates a strong relative intensity (60% to 80%), "m" indicates an intermediate relative intensity (40% to 60%), and "w" indicates a weak relative intensity (0% to 40%). In Table 4, the peak intensity (%) refers to a relative intensity when the peak intensity of the maximum peak in the diffraction pattern is set to 100.

TABLE 3

| Location of peak 2θ (°) | Relative intensity |
|---|---|
| 6.36-6.56 | m-w |
| 6.67-6.87 | m-w |
| 7.93-8.23 | w |
| 8.55-8.85 | m-w |
| 9.47-9.77 | s, m, w |
| 10.59-10.89 | w |
| 13.43-13.73 | w |
| 14.60-14.90 | w |
| 15.67-15.97 | w |
| 17.23-17.53 | w |
| 19.29-19.59 | m-w |
| 19.73-20.03 | w |
| 20.27-20.67 | w |
| 20.75-21.15 | w |
| 21.41-21.81 | vs |
| 21.53-21.93 | s |
| 22.29-22.69 | s-m |
| 22.79-23.19 | s |
| 23.09-23.49 | w |
| 25.52-25.92 | w |
| 25.90-26.30 | m-w |
| 26.16-26.56 | w |
| 26.57-27.07 | w |
| 27.24-24.64 | m |
| 27.87-28.37 | w |
| 28.51-29.01 | w |
| 28.90-29.40 | w |

TABLE 3-continued

| Location of peak 2θ (°) | Relative intensity |
|---|---|
| 29.47-29.97 | w |
| 29.96-30.46 | m-w |
| 30.53-31.03 | m-w |

TABLE 4

| Location of peak 2θ (°) | Peak intensity (%) |
|---|---|
| 6.36-6.56 | 28-55 |
| 6.67-6.87 | 34-51 |
| 7.93-8.23 | 24-38 |
| 8.55-8.85 | 20-48 |
| 9.47-9.77 | 33-61 |
| 10.59-10.89 | 16-31 |
| 13.43-13.73 | 16-24 |
| 14.60-14.90 | 12-17 |
| 15.67-15.97 | 9-14 |
| 17.23-17.53 | 10-16 |
| 19.29-19.59 | 38-52 |
| 19.73-20.03 | 22-37 |
| 20.27-20.67 | 17-24 |
| 20.75-21.15 | 14-22 |
| 21.41-21.81 | 100 |
| 21.53-21.93 | 68-87 |
| 22.29-22.69 | 53-67 |
| 22.79-23.19 | 72-89 |
| 23.09-23.49 | 19-25 |
| 25.52-25.92 | 18-28 |
| 25.90-26.30 | 27-42 |
| 26.16-26.56 | 20-27 |
| 26.57-27.07 | 17-37 |
| 27.24-24.64 | 42-56 |
| 27.87-28.37 | 23-34 |
| 28.51-29.01 | 14-24 |
| 28.90-29.40 | 18-36 |
| 29.47-29.97 | 15-29 |
| 29.96-30.46 | 19-41 |
| 30.53-31.03 | 22-41 |

The beta-type zeolite is preferably manufactured by dealuminating a beta-type zeolite having a substantially octahedral shape and a low Si/Al ratio. Meanwhile, the MSE-type zeolite is preferably manufactured by dealuminating a MSE-type zeolite having a low Si/Al ratio. Specifically, a preferable manufacturing method of the beta-type zeolite of the invention includes three processes of (1) an ion exchange treatment process of a raw material beta-type zeolite, (2) a process of exposing the ion-exchanged raw material beta-type zeolite to water vapor, and (3) an acid treatment process of the raw material beta-type zeolite which has been exposed to water vapor. A preferable manufacturing method of the MSE-type zeolite of the invention is the same as above. Therefore, hereinafter, the manufacturing method of a zeolite of the invention will be described using the preferably manufacturing method of the beta-type zeolite as an example.

(1) The Ion Exchange Treatment Process of a Raw Material Beta-Type Zeolite

The raw material beta-type zeolite generally includes an alkali metal such as sodium. Since the beta-type zeolite including an alkali metal has a difficulty in exhibiting desired characteristics in a case in which the zeolite is used as a catalyst in the petrochemical industry or a hydrocarbon trap for purifying the exhaust gas of an internal-combustion engine, the alkali metal included in the raw material beta-type zeolite is removed through ion exchange, and the zeolite is transformed into an ammonium-type beta-type zeolite.

The raw material beta-type zeolite which is subjected to an ion exchange treatment has a low Si/Al ratio of, for example, 4 to 100, preferably 4 to 8, and more preferably 5 to 7. This is because it is easy to synthesize a beta-type zeolite having the above low Si/Al ratio as a beta-type zeolite having a substantially octahedral shape.

As a result of studies by the inventors, it was found that it is advantageous to use a beta-type zeolite synthesized without using the organic SDA (hereinafter also referred to as "OSDA-free beta-type zeolite") as the raw material beta-type zeolite. When the OSDA-free beta-type zeolite is used as the raw material beta-type zeolite, it is easy to synthesize a beta-type zeolite having a substantially octahedral shape. In addition, even when the OSDA-free beta-type zeolite having a low Si/Al ratio is dealuminated, the substantially octahedral shape is maintained, and the catalytic activity of the obtained beta-type zeolite having a high Si/Al ratio is not easily deactivated. Furthermore, use of the OSDA-free beta-type zeolite is advantageous since the organic SDA is not used, and is also advantageous from the viewpoint of economic efficiency and environmental load.

Meanwhile, as a result of studies by the inventors, it is found that the OSDA-free beta-type zeolite has a crystal structure which is easily broken when the Si/Al is increased using a method of the related art, for example, the method described in Patent Citation 3 described above. However, when the OSDA-free beta-type zeolite is treated using the present manufacturing method, the breaking of the crystal structure is extremely suppressed so that the Si/Al can be increased.

As a synthesizing method of the OSDA-free beta-type zeolite, it is possible to employ, for example, the method described in the pamphlet of the International Publication No. 2011/013560. In addition, it is possible to employ the method described in the specification of Chinese Patent Application Laid-Open No. 101249968A. Furthermore, it is also possible to employ the method described in Chemistry of Materials, Vol. 20, No. 14, p. 4533 to 4535 (2008).

An example of the synthesizing method of the OSDA-free beta-type zeolite is as follows.

(i) A silica source, an alumina source, an alkali source and water are mixed so as to form a reaction mixture having a composition indicated by the molar ratios shown below, $SiO_2/Al_2O_3$=40 to 200, particularly 44 to 200
$Na_2O/SiO_2$=0.22 to 0.4, particularly 0.24 to 0.35
$H_2O/SiO_2$=10 to 50, particularly 15 to 25

(ii) A beta-type zeolite not including an organic compound which has a $SiO_2/Al_2O_3$ ratio of 8 to 30 and an average particle diameter of 150 nm or more, particularly, 150 nm to 1000 nm, and more particularly 200 nm to 600 nm, is used as a seed crystal, the beta-type zeolite is added to the reaction mixture at a proportion of 0.1 mass % to 20 mass % with respect to the silica component in the reaction mixture, and (iii) the reaction mixture to which the seed crystal is added is enclosure-heated at 100° C. to 200° C., particularly 120° C. to 180° C.

In the ion exchange of the raw material beta-type zeolite, an ammonium compound is used, and, particularly, use of ammonium nitrate, ammonium chloride, ammonium acetate or ammonium sulfate is preferable. In a case in which the ion exchange is carried out using an ammonium compound, such as ammonium nitrate or ammonium chloride, an aqueous solution having a concentration of ammonium ion of 0.1 mol/L to 10 mol/L is preferably added to 10 g of the raw material beta-type zeolite at 25 mL to 1000 mL, preferably at 100 mL to 1000 mL, and particularly at 400 mL to 600 mL. The ion exchange can be carried out in a state in which the aqueous solution including ammonium ions is heated or not heated. In a case in which the aqueous solution including ammonium ions is heated, the heating temperature is set to 40° C. to 100° C., and particularly preferably set to 70° C. to 90° C. The raw material beta-type zeolite is dispersed in the aqueous solution including ammonium ions so as to form a dispersion liquid, and this state is held for a predetermined time, thereby carrying out the ion exchange. The holding time is set to 1 hour to 48 hours, and particularly preferably set to 12 hours to 24 hours. The dispersion liquid may be in a static state or in a stirred state.

After the dispersion liquid is held for a predetermined time, the dispersion liquid is filtered, the raw material beta-type zeolite is separated, and water washing is carried out. If necessary, a combination of the ion exchange treatment and water washing may be repeated a plurality of times. After the ion exchange treatment is carried out in the above manner, the raw material beta-type zeolite is dried, and an ammonium-type beta-type zeolite is obtained. This ammonium-type beta-type zeolite has, accordingly, an extremely reduced content of alkali metal ions.

(2) A Process of Exposing the Ion-Exchanged Raw Material Beta-Type Zeolite to Water Vapor In order to expose the ammonium-type raw material beta-type zeolite to water vapor, for example, the raw material beta-type zeolite may be statically placed in a water vapor atmosphere, or the raw material beta-type zeolite may be disposed in a water vapor stream. Specifically, it is possible to expose the raw material beta-type zeolite to water vapor using an apparatus shown in FIG. 1. The apparatus 10 shown in the same drawing has a holding tube 11 in which the raw material beta-type zeolite is held. Both ends of the holding tube 11 are opened. The bottom end portion 11a is open to the atmosphere. The top end portion 11b of the holding tube 11 serves as an inlet of water vapor, and is connected to a water vapor supply source 12 and an inert gas supply source 13. The water vapor supply source 12 is configured of a bottomed chassis 12a opened at the top end portion. An end portion of a bubbling tube 12b of inert gas is inserted into the chassis 12a. The other end portion of the bubbling tube 12b is connected to the inert gas supply source (not shown in the drawing). Furthermore, water 14 is stored in the chassis 12a. The height of water surface is higher than the location of the end portion of the bubbling portion 12b which is inserted into the bottomed chassis 12a. Heating means 15 is disposed around the holding tube 11. The heating means 15 can heat the raw material beta-type zeolite held in the holding tube 11 and water vapor circulating in the holding tube 11. An inert gas, such as argon, is supplied from the inert gas supply source 13, and the inert gas is bubbled through the bubbling tube 12b in the water vapor supply source 12, thereby supplying a predetermined amount of water vapor to the holding tube 11. The supply amount of water vapor is determined by the balance of the supply amount of the inert gas in the inert gas supply source 13 and the water vapor supply source 12. Water vapor supplied to the holding tube 11 is heated by using the heating means 15 along with the raw material beta-type zeolite. In addition, the raw material beta-type zeolite is exposed to water vapor heated to a predetermined temperature. It is considered that this exposure detaches aluminum atoms which compose the raw material beta-type zeolite from predetermined sites in the crystal lattice, and silicon atoms migrate into the detached sites. However, at a point in time when the raw material beta-type zeolite is exposed to water vapor, the Si/Al ratio in the raw material beta-type zeolite is not changed. In addition, when the raw material beta-type zeolite is exposed to water vapor, the zeolite is transformed from the ammonium type to a proton type.

The temperature of the water vapor used for the exposure of the raw material beta-type zeolite is preferably set to 150° C. to 1000° C., more preferably set to 500° C. to 900° C., and particularly preferably set to 500° C. to 800° C. since it is possible to accelerate detachment of aluminum while suppressing breaking of the crystal structure of the zeolite. For the same reason, in a case in which the temperature of the water vapor is within the above range, the exposure time of the water vapor is preferably set to 1 hour to 48 hours, more preferably set to 1 hour to 24 hours, and particularly preferably set to 12 hours to 24 hours. The pressure (partial pressure) of the water vapor at a point in time when the raw material beta-type zeolite and the water vapor come into contact is the atmospheric pressure or lower since the bottom end portion of the holding tube 11 is open. The preferable partial pressure of the water vapor is 1 kPa to 101.3 kPa.

(3) An Acid Treatment Process of the Raw Material Beta-Type Zeolite which has been Exposed to Water Vapor The raw material beta-type zeolite which has been exposed to water vapor is subjected to an acid treatment, which generates dealuminum from the beta-type zeolite. As the acid used in the acid treatment, a variety of mineral acids are preferably used. For example, it is possible to use a nitric acid, a sulfuric acid, a hydrochloric acid or the like. As the concentration of the acid increases when the acid treatment is carried out, dealumination proceeds so that the Si/Al ratio of the beta-type zeolite increases. Therefore, in order to obtain a beta-type zeolite having a desired Si/Al ratio, it is a simple means to adjust the concentration of the acid. From the above viewpoint, while varying depending on the kind of the acid used, in many cases, the concentration of the acid is preferably 0.1 mass % to 100 mass %, and particularly preferably 0.1 mass % to 60 mass %. For example, in a case in which a nitric acid is used as the mineral acid, the concentration of the nitric acid is preferably 0.1 mass % to 70 mass %, and particularly preferably 0.5 mass % to 5 mass %. In a case in which a nitric acid is used as the mineral acid, the concentration of the nitric acid is preferably 0.01 mol/L to 21 mol/L, and particularly preferably 0.05 mol/L to 14 mol/L in terms of a mole concentration. Meanwhile, when the concentration of the acid is high, while dealumination proceeds as described above, accordingly, the crystal structure of the zeolite is liable to be broken. Particularly, in a case in which the OSDA-free beta-type zeolite is used as the raw material, the crystal structure is liable to be broken. However, in the invention, since the water vapor exposure treatment is carried out prior to the acid treatment, even in a case in which the OSDA-free beta-type zeolite is used as the raw material, and the treatment is carried out using an acid having a high concentration, the crystal structure of the zeolite is not easily broken.

The amount of the acid used in the acid treatment is 5 mL to 500 mL, preferably 10 mL to 500 mL, and particularly preferably 100 mL to 200 mL per 1 gram of the raw material beta-type zeolite when the acid has the above concentration since efficient dealumination is caused. The acid treatment may be carried out with heating or without heating. In a case in which the acid treatment is carried out with heating, the temperature of the acid is preferably set to 40° C. to 100° C., and particularly preferably set to 70° C. to 90° C. in terms of efficient dealumination. In a case in which a nitric acid is used as the mineral acid, while depending on the concentration, the temperature of the nitric acid is preferably set to 40° C. to 130° C., particularly preferably set to 70° C. to 130° C., and more particularly preferably set to 70° C. to 90° C. In addition, in a case in which the acid treatment is carried out with heating, the acid may be in a refluxed state. In a case in which the concentration and temperature of the acid are within the above ranges, the time of the acid treatment is preferably set to 1 hour to 24 hours, and particularly preferably set to 2 hours to 24 hours since the breaking of the crystal structure of the zeolite is suppressed, and efficient dealumination is carried out.

After the acid treatment is completed, solid-liquid separation is carried out, the separated beta-type zeolite is washed with water once or a plurality of times, and then dried. In this manner, a target beta-type zeolite is obtained. The beta-type zeolite obtains an increased Si/Al ratio compared to the OSDA-free beta-type zeolite which is used as the raw material. The beta-type zeolite has the above increased Si/Al ratio, and also maintains the crystal structure. Furthermore, the beta-type zeolite maintains the substantially octahedral shape of the OSDA-free beta-type zeolite. This beta-type zeolite has been transformed into a proton-type zeolite as described above.

A preferable manufacturing method of the MSE-type zeolite of the invention is the same as the above preferable manufacturing method of the beta-type zeolite except that a raw material MSE-type zeolite is used instead of the raw material beta-type zeolite, and a zeolite synthesized without using the organic SDA (hereinafter also referred to as "OSDA-free MSE-type zeolite") is used as the raw material MSE-type zeolite in the above preferable manufacturing method of the beta-type zeolite.

As a synthesizing method of the OSDA-free MSE-type zeolite, it is possible to employ, for example, the method described in the pamphlet of the International Publication No. 2012/002367. An example of the synthesizing method of the OSDA-free beta-type zeolite is as follows.

(i) A silica source, an alumina source, an alkali source and water are mixed so as to form a reaction mixture having a composition indicated by the molar ratios shown in the following (a) or (b), (a)
$SiO_2/Al_2O_3$=40 to 200, particularly 44 to 200
$(Na_2O+K_2O)/SiO_2$=0.24 to 0.4, particularly 0.25 to 0.35
$K_2O/(Na_2O+K_2O)$=0 to 0.7, particularly 0.01 to 0.65
$H_2O/SiO_2$=10 to 50, particularly 15 to 25
(b)
$SiO_2/Al_2O_3$=10 to 40, particularly 12 to 40
$(Na_2O+K_2O)/SiO_2$=0.05 to 0.25, particularly 0.1 to 0.25
$K_2O/(Na_2O+K_2O)$=0 to 0.7, particularly 0.01 to 0.65
$H_2O/SiO_2$=5 to 50, particularly 10 to 25

(ii) A MSE-type zeolite not including an organic compound which has a $SiO_2/Al_2O_3$ ratio of preferably 10 to 50, particularly preferably 15 to 40, and an average particle diameter of preferably 100 nm to 2000 nm, more preferably 200 nm to 1000 nm, is used as a seed crystal, the beta-type zeolite is added to the reaction mixture at a proportion of preferably 0.1 mass % to 30 mass %, more preferably 1 mass % to 20 mass %, and still more preferably 1 mass % to 10 mass % with respect to the silica component in the reaction mixture, and (iii) the reaction mixture to which the seed crystal is added is enclosure-heated at 100° C. to 200° C., particularly at 120° C. to 180° C.

As is evident from the compositions of the above (a) and (b), a gel used to manufacture the MSE-type zeolite may include only sodium ions as the alkali metal, or may include both sodium ions and potassium ions. When a zeolite is synthesized using a gel including sodium ions and potassium ions, compared to a case in which a zeolite is synthesized using a gel including only sodium ions, it is advantageous since the by-production of impurities, particularly, the generation of a small amount of a byproduct zeolite, can be further prevented. The MSE-type zeolite can be synthesized from a gel including only potassium ions, when the proportion of potassium ions increases, there is a tendency that the crystallization rate becomes slow and the degree of crystallinity of the obtained MSE-type zeolite becomes low. As a potassium ion source, for example, potassium hydroxide is preferably used. In addition, in order to adjust the $K_2O/(Na_2O+K_2O)$ ratio, as a potassium source other than the above, a potassium salt, such as potassium chloride, potassium sulfate or potassium nitrate, may be used.

The beta-type zeolite and the MSE-type zeolite of the invention, which are obtained in the above manners, are promising substances as a solid acid catalyst or an adsorbent, and, in more detail, are particularly promising as a catalyst that catalytically cracks paraffin, for example, a cracking catalyst of a long-chain hydrocarbon (for example, hexane) in the petrochemical industry. Also, the beta-type zeolite and the MSE-type zeolite are promising substances as a hydrocarbon trap for purifying the exhaust gas from an internal-combustion engine.

Thus far, the invention has been described based on the preferable embodiments, but the invention is not limited to the embodiments. For example, according to the above manufacturing method, it is possible to preferably manufacture the beta-type zeolite and the MSE-type zeolite of the invention; however, depending on the manufacturing method, it is also possible to manufacture beta-type zeolites and MSE-type zeolites other than the beta-type zeolite and the MSE-type zeolite of the invention.

EXAMPLES

Hereinafter, the invention will be described in more detail using examples. However, the scope of the invention is not limited to the examples. Unless otherwise described, "%" indicates "mass %".

Example 1

(1) Synthesis of a Seed Crystal

A beta-type zeolite having a $SiO_2/Al_2O_3$ ratio of 24.0 was synthesized by carrying out stirring and heating at 165° C. for 96 hours using a well-known method of the related art in which tetraethylammonium hydroxide was used as the organic SDA, sodium aluminate was used as the alumina source, and fine powder-form silica (Mizukasil P707) was used as the silica source. The beta-type zeolite was fired at 550° C. for 10 hours in an electric furnace while circulating air, thereby manufacturing a crystal not including an organic substance. As a result of observing the crystal using a scanning electron microscope, the average particle diameter was 280 nm. The crystal of the beta-type zeolite not including an organic substance was used as the seed crystal.

(2) Synthesis of an OSDA-Free Beta-Type Zeolite

Figure 2:
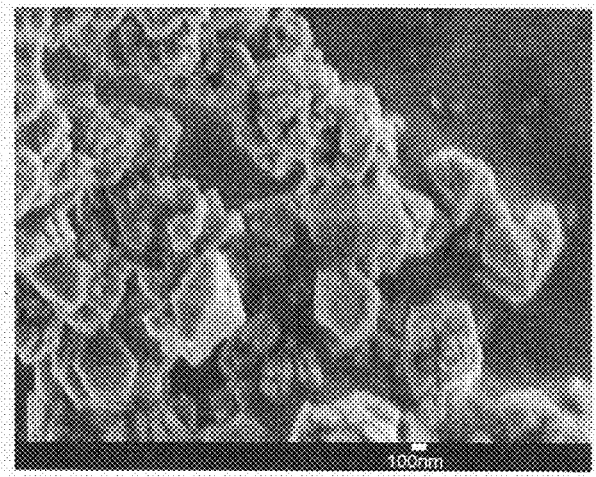
FIG. 2A is a scanning electron microscopic photograph of a beta-type zeolite synthesized without using an organic structure directing agent.
FIG. 2B is a scanning electron microscopic photograph of the beta-type zeolite shown in FIG. 2A after dealumination (Example 1).
Figure 2:
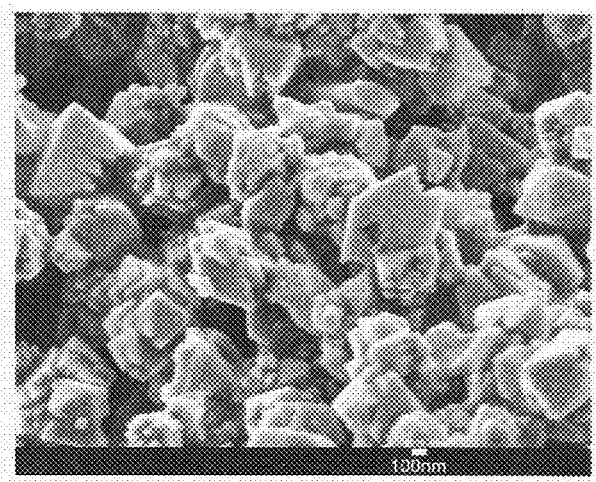

Sodium aluminate (0.235 g) and 36% sodium hydroxide (1.828 g) were dissolved in pure water (13.9 g). A mixture of fine powder-form silica (Cab-O-sil, M-5, 2.024 g) and the above seed crystal (0.202 g) was added to the aqueous solution little by little, stirred and mixed, thereby producing a reaction mixture. In the reaction mixture, the $SiO_2/Al_2O_3$ ratio was 70, the $Na_2O/SiO_2$ ratio was 0.3, and the $H_2O/SiO_2$ ratio was 20. This reaction mixture was put into a 60 mL stainless steel closed vessel, and statically heated at 140° C. for 34 hours under an autogenous pressure without aging and stirring. After the vessel was cooled, the product was filtered and washed with warm water, thereby obtaining a white powder. As a result of carrying out an X-ray diffraction measurement on this product, it was confirmed that the beta-type zeolite did not include impurities. As a result of a composition analysis, the Si/Al ratio was 6.4. A scanning electron microscopic photograph of the beta-type zeolite is shown in FIG. 2A. As shown in the same drawing, it is found that the beta-type zeolite has a substantially octahedral shape.

(3) Ion Exchange Treatment

The obtained OSDA-free beta-type zeolite was used as the raw material, and was dispersed in an aqueous solution of ammonium nitrate. The mass ratio of the OSDA-free beta-type zeolite, ammonium nitrate, and water was set to 1:2:50. This dispersion liquid was statically placed over 24 hours in a state of being heated at 80° C., thereby carrying out ion exchange. After that, filtration was carried out so as to separate the beta-type zeolite. After the operation of ion exchange and filtration was repeated one more time, the resultant was washed with water, and dried at 80° C., thereby producing an ammonium-type beta-type zeolite.

(4) Exposure Using Water Vapor

The ammonium-type beta-type zeolite was filled into an apparatus shown in FIG. 1. The filling amount was set to 1 g. A gas mixture of argon and water vapor was continuously circulated for 24 hours in a state in which the ammonium-type beta-type zeolite was heated to 700° C. by the heating means 15 shown in the same drawing. The partial pressure of the water vapor was set to 12.2 kPa. The exposure using water vapor transformed the beta-type zeolite from the ammonium-type into a proton-type.

(5) Acid Treatment

Figure 3:
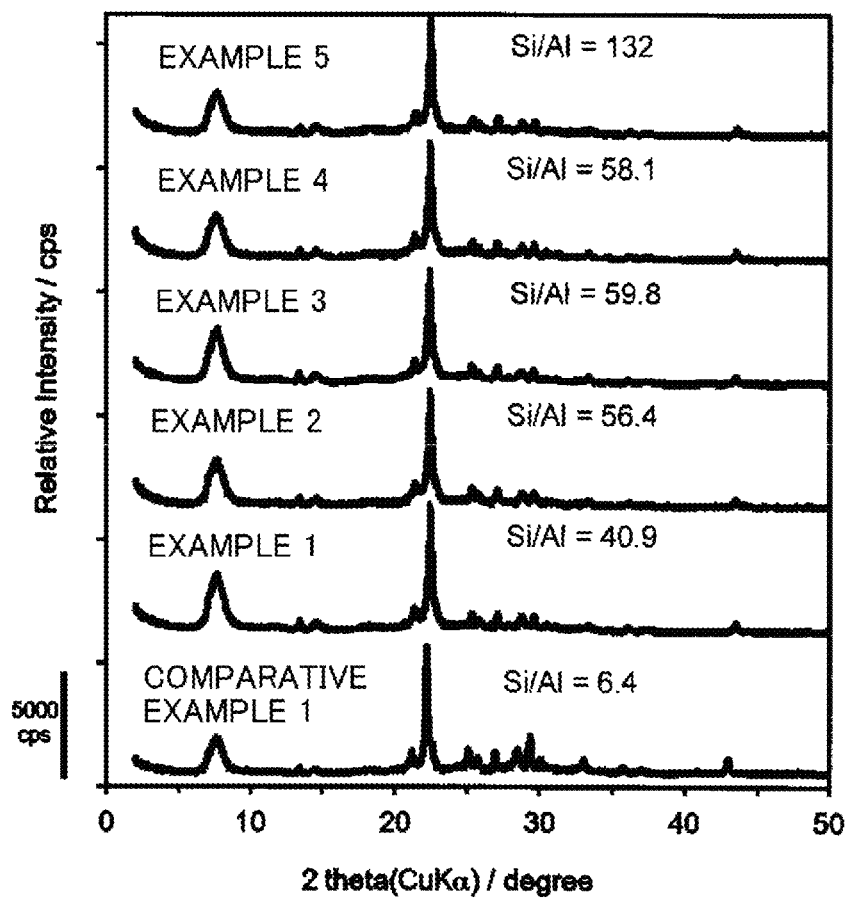
FIG. 3 shows X-ray diffraction diagrams of beta-type zeolites obtained in Examples 1 to 5 and Comparative example 1.

The water vapor-exposed beta-type zeolite was subjected to an acid treatment using a 0.1 mol/L aqueous solution of nitric acid. The temperature of the aqueous solution of nitric acid was set to 80° C. The aqueous solution of nitric acid (10 mL) was added to the beta-zeolite (0.1 g). The treatment was carried out for 2 hours while stirring the solution by using a magnetic stirrer. In the above manner, a target beta-type zeolite was obtained. A scanning electron microscopic photograph of the obtained beta-type zeolite is shown in FIG. 2B. In addition, the X-ray diffraction diagram is shown in FIG. 3. Furthermore, the Si/Al ratio obtained from an element analysis was shown in FIG. 3. As shown in FIG. 2B, it is found that the beta-type zeolite has a substantially octahedral shape.

Examples 2 to 5

The concentrations of the aqueous solution of nitric acid used in the acid treatment of Example 1 were set to 0.5 mol/L (Example 2), 1.0 mol/L (Example 3), 2.0 mol/L (Example 4), and 8.0 mol/L (Example 5). Except the above, beta-type zeolites having an increased Si/Al ratio were obtained in the same manner as in Example 1. The X-ray diffraction diagrams of the obtained beta-type zeolites are shown in FIG. 3. In addition, the Si/Al ratios obtained from element analyses were shown in FIG. 3. Meanwhile, while not shown, the beta-type zeolites obtained in the above examples had a substantially octahedral shape. In addition, for the beta-type zeolite obtained in Example 3, the BET specific surface area and the volume of the micro hole were measured under the following conditions. The BET specific surface area obtained through the measurement was 617 m²/g, and the volume of the micro hole was 0.17 cm³/g.

(Measurement Conditions of the BET Specific Surface Area and the Volume of the Micro Hole)

Apparatus used: Belsorp-max-1-N, apparatus for automatic adsorption measurement manufactured by Bel Japan, Inc.

Measurement temperature: −196° C. (nitrogen), Temperature of an air constant-temperature bath: 40° C.

Equilibrium adsorption time: 300 s

Sample prior treatment conditions: a heating treatment (400° C., 2 h) in a vacuum ($1.33 \times 10^{-4}$ Pa)

Comparative Example 1

A proton-type beta-type zeolite was obtained by carrying out a direct thermal treatment without carrying out the exposure using water vapor and the acid treatment after ion-exchanging the OSDA-free beta-type zeolite in Example 1. The conditions of the thermal treatment were set to a temperature of 650° C., a time of 60 minutes, and an air circulation amount of 40 cm³/min. The X-ray diffraction diagram of the obtained beta-type zeolite is shown in FIG. 3. In addition, the Si/Al ratio obtained from an element analysis was shown in the same drawing. The beta-type zeolite lost the octahedral shape due to the thermal treatment.

Comparative Example 2

(1) Synthesis of a Beta-Type Zeolite Using the Organic SDA (OSDA)

Figure 4:
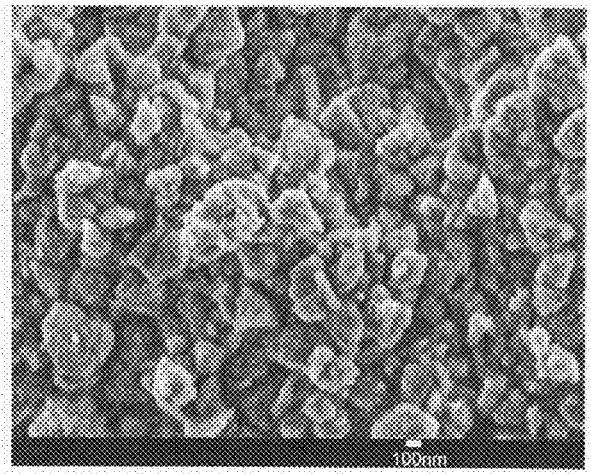
FIG. 4A is a scanning electron microscopic photograph of a beta-type zeolite synthesized using an organic structure directing agent.
FIG. 4B is a scanning electron microscopic photograph of the beta-type zeolite shown in FIG. 4A after dealumination (Comparative example 3).
Figure 4:
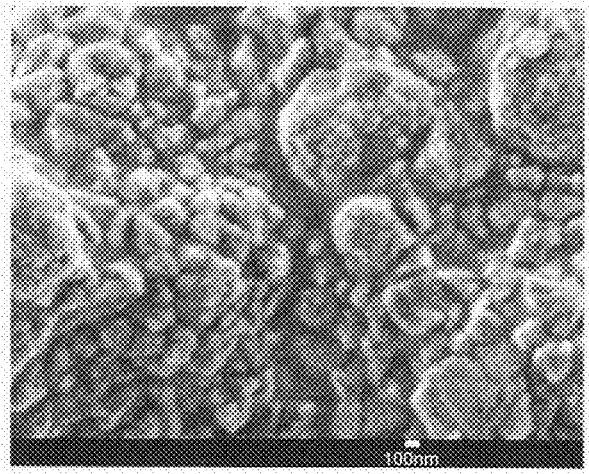

Tetraethylammonium hydroxide as the organic structure directing agent (OSDA) and an aqueous solution including sodium hydroxide were stirred at room temperature, and colloidal silica was added thereto. As the colloidal silica, Ludox HS-40 (silica portion 40%) was used. After 30 minutes of stirring from the addition of the colloidal silica, an aqueous solution of aluminum sulfate was added, and, furthermore, stirring was carried out for 30 minutes, thereby producing a gel. The composition of the gel was 0.033 mole of $Al_2O_3$, 0.24 mole of sodium hydroxide, 0.50 mole of tetraethylammonium hydroxide, and 20 mole of water with respect to 1 mole of $SiO_2$. This gel was put into an autoclave, and the reaction was performed over 7 days in a state of being heated to 150° C. In the above manner, a beta-type zeolite was obtained. This zeolite was heated at 550° C. for 6 hours in the atmosphere so as to decompose and remove tetraethylammonium hydroxide which was the OSDA. As a result of carrying out an X-ray diffraction measurement, it was confirmed that this product was a beta-type zeolite not including impurities. As a result of a composition analysis, the Si/Al was 13.1. A scanning electron microscopic photograph of the beta-type zeolite is shown in FIG. 4A. As shown in the same drawing, it is found that the beta-type zeolite has an irregular shape.

(2) Ion Exchange

Figure 5:
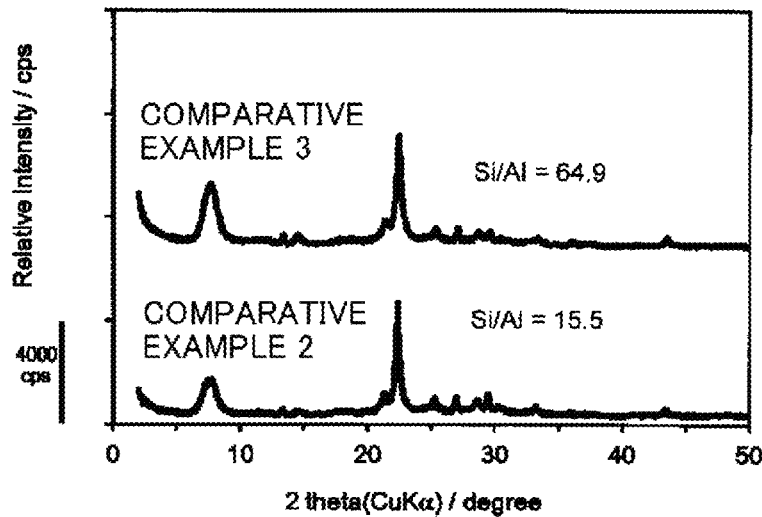
FIG. 5 shows X-ray diffraction diagrams of beta-type zeolites obtained in Comparative examples 2 and 3.

Ion exchange was carried out under the same conditions as in Example 1. The exposure using water vapor and the acid treatment were not carried out. After the ion exchange, a thermal treatment was carried out at a temperature of 650° C. for a time of 60 minutes and at an air circulation amount of 40 cm³/min, thereby transforming the beta-type zeolite into a proton type. In the above manner, a beta-type zeolite was obtained. The X-ray diffraction diagram of the obtained beta-type zeolite is shown in FIG. 5. In addition, the Si/Al ratio obtained from an element analysis was shown in the same drawing.

Comparative Example 3

In Comparative example 2, the exposure using water vapor and the acid treatment were carried out under the same conditions as in Example 3 after the ion exchange. In the above manner, a beta-type zeolite was obtained. A scanning electron microscopic photograph of the obtained beta-type zeolite is shown in FIG. 4B. In addition, the X-ray diffraction diagram is shown in FIG. 5. Also, the Si/Al ratio obtained from an element analysis was shown in FIG. 5. As shown in FIG. 4B, it is found that this beta-type zeolite has an irregular shape.

(Evaluation)

For the beta-type zeolites obtained in Example 3 and Comparative examples 1 to 3, Evaluation 1 and Evaluation 2 of the catalytic activity during the cracking reaction of hexane were carried out in the following order. Prior to Evaluation 1 and Evaluation 2, powder-form beta-type zeolite was molded and granulated. Specifically, beta-type zeolite powder (1 g to 2 g) was filled into a tablet die having an inner diameter of 20 mm, and then pressure-molded using an hydraulic press at 0.4 MPa, thereby producing a pellet having a diameter of 20 mm. This pellet was ground to an appropriate extent on a sieve, granulated into 500 µm to 600 µm, and used as a catalyst.

(Evaluation 1)

Figure 6:
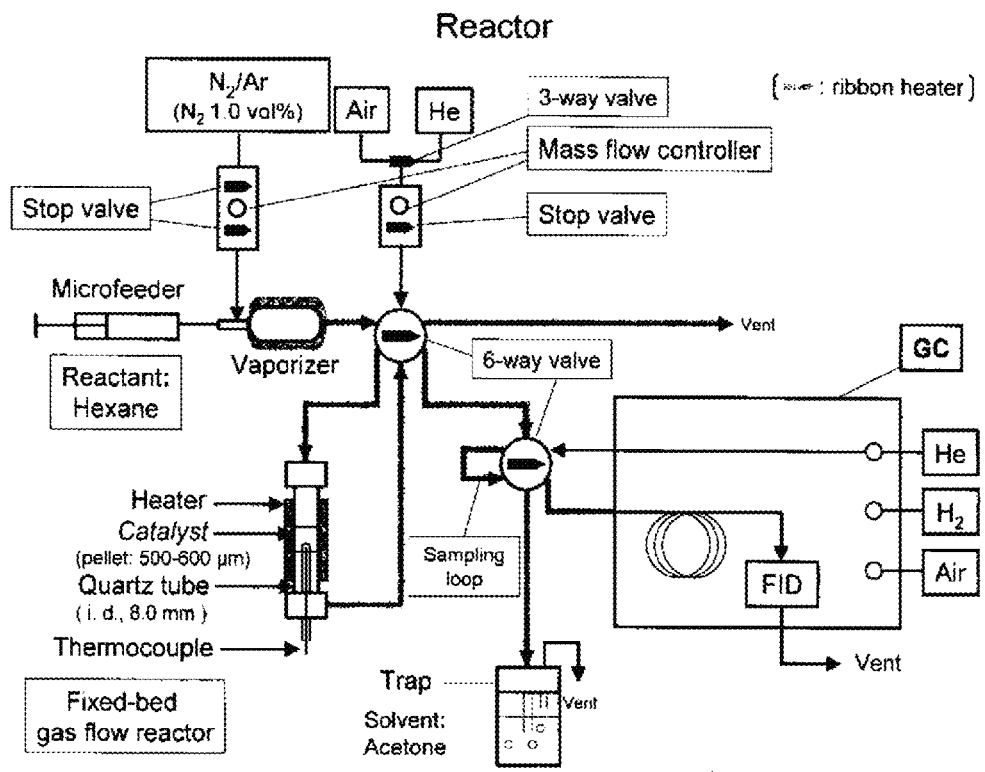
FIG. 6 is a schematic view of an apparatus for evaluating the catalytic activity of the beta-type zeolite.

A catalytic reaction was carried out using a fixed-bed normal pressure circulation reaction apparatus. The schematic view of the apparatus is shown in FIG. 6. Hexane, which was a reactant, was supplied from a syringe using a syringe pump, and introduced into a nitrogen (1%)-argon gas mixture, which was a carrier gas. Since the hexane supplied from the syringe pump was introduced into a vaporizing chamber heated in advance, the hexane was vaporized so as to become gas, and this gas was made to accompany the carrier gas. The condensation of the vaporized hexane was prevented by heating the gas line of a reaction apparatus from the outside at an appropriate temperature using a stainless steel pipe having an inner diameter of 2 mm and a heater. A quartz tube having an inner diameter of 8 mm was used as a reaction tube, the previously granulated beta-type zeolite catalyst (100 mg) was filled into the quartz tube, and a catalyst layer was held at the central portion of the reaction tube using silica wool. As a reaction pretreatment, the temperature of the beta-type zeolite catalyst was increased up to 650° C. at a temperature-increase rate of 7° C./min under air circulation, and the beta-type zeolite was held for 1 hour in this atmosphere. After that, the circulated gas was switched to helium, and then the temperature of the reaction tube was decreased to 450° C. at 5° C./min. After it was confirmed that the beta-type zeolite was stabilized at 450° C., a methane-helium gas mixture accompanied by hexane was supplied to the catalyst layer, and a catalytic reaction was begun. The partial pressure of the hexane was 5.0 kPa. After 5 minutes elapsed from the beginning of the reaction, a hexagonal valve was switched so as to introduce reaction products stored in a sampling roof into a gas chromatograph, the reaction products were separated by using a capillary column, and the properties and quantities of the respective products and unreacted substances were measured by using a flame ionization detector (FID). After a predetermined time (70 minutes) elapsed, the supply of hexane to the catalyst layer was stopped, and the circulated gas was switched to helium. After that, the temperature was increased up to 500° C. at 1° C./min to 2° C./min, the hexane was supplied again when the temperature was stabilized, and the catalytic reaction was carried out. The same operation was subsequently carried out at 550° C. an 600° C. The W/F during the catalytic reaction was set to 19.8 g-catalyst h (mol-hexane)$^{-1}$ in all reaction temperatures. After the catalytic reaction at 600° C. was stopped, the beta-type zeolite was naturally cooled under helium circulation. The results are shown in Table 5 and FIG. 7 below. The selection rates into the respective products were obtained based on carbon (carbon atom-converted). The propylene ($C_3$=) yield was obtained from "the inversion rate× the selection rate into propylene ($C_3$=)". Meanwhile, the reaction temperature was measured between the heater installed so as to heat the quartz reaction tube of the fixed-bed normal pressure circulation reaction apparatus from the outside, and the reaction tube.

Example 3 is used as a catalyst, and cracking of hexane is carried out, $C_3$=(propylene), which is a useful substance as a chemical raw material, is generated at a high yield. In addition, it is also found that deactivation of the beta-type zeolite is not observed. In contrast to the above, in the beta-type zeolite of Comparative example 1, which had a substantially octahedral shape, but had a low Si/Al ratio, and the beta-type zeolite of Comparative example 2, which had a high Si/Al ratio, but had an irregular shape, the yields of $C_3$=(propylene) were lower than that of Example 3. Furthermore, deactivation was observed. In the beta-type zeolite of Comparative example 3, which had an extremely high Si/Al ratio, but had an irregular shape, the yield of $C_3$=(propylene) was favorable, but aging deactivation was observed in the reaction at 600° C.

TABLE 5

| Catalyst | Temperature (° C.) | TOS (min) | Inversion rate (%) | Selection rate into the respective products (mol %) | | | | | | | | Substance yield (%) | $C_3$ = yield (C %) |
| --- | --- | --- | --- | --- | --- | --- | --- | --- | --- | --- | --- | --- | --- |
| | | | | $C_1$ | $C_2$= | $C_2$ | $C_3$= | $C_3$ | $C_4$ | $C_5$ | Aromatic | | |
| Example 3 | 450 | 5 | 8.3 | 4.1 | 6.7 | 9.4 | 47.2 | 20.5 | 12.2 | 0.0 | 0.0 | 97.0 | 4.0 |
| | 500 | 5 | 20.1 | 4.7 | 8.9 | 9.3 | 45.8 | 17.7 | 12.7 | 0.7 | 0.2 | 99.6 | 9.6 |
| | 550 | 5 | 51.3 | 6.5 | 12.6 | 7.8 | 45.8 | 14.3 | 11.7 | 0.5 | 0.8 | 98.1 | 24.5 |
| | 600 | 5 | 85.1 | 12.2 | 19.6 | 6.0 | 39.9 | 12.0 | 8.1 | 0.3 | 1.9 | 91.2 | 35.0 |
| Comparative example 1 | 450 | 5 | 54.0 | 2.8 | 10.5 | 2.0 | 24.9 | 40.8 | 15.7 | 1.6 | 1.8 | 91.2 | 11.9 |
| | 500 | 5 | 57.1 | 6.0 | 14.3 | 5.1 | 30.0 | 28.0 | 13.1 | 0.6 | 2.8 | 89.0 | 15.6 |
| | 550 | 5 | 56.0 | 8.0 | 15.4 | 6.2 | 37.7 | 17.6 | 11.1 | 0.3 | 3.7 | 85.5 | 18.9 |
| | 600 | 5 | 47.4 | 10.5 | 18.1 | 6.3 | 40.1 | 8.6 | 10.1 | 0.2 | 6.0 | 83.1 | 16.7 |
| Comparative example 2 | 450 | 5 | 60.3 | 2.9 | 10.5 | 2.1 | 22.2 | 41.8 | 16.9 | 1.6 | 1.9 | 95.1 | 12.4 |
| | 500 | 5 | 64.4 | 6.5 | 14.1 | 5.5 | 26.5 | 31.9 | 12.2 | 0.5 | 2.8 | 91.7 | 16.1 |
| | 550 | 5 | 76.9 | 10.5 | 17.8 | 7.5 | 27.4 | 22.7 | 9.1 | 0.3 | 4.7 | 85.0 | 19.2 |
| | 600 | 5 | 74.3 | 12.6 | 21.1 | 7.4 | 33.5 | 11.3 | 6.5 | 0.1 | 7.5 | 88.9 | 24.0 |
| Comparative example 3 | 450 | 5 | 7.5 | 4.0 | 6.0 | 10.1 | 49.2 | 20.2 | 10.5 | 0.0 | 0.0 | 93.7 | 3.6 |
| | 500 | 5 | 19.0 | 4.4 | 7.3 | 9.3 | 46.8 | 17.0 | 12.4 | 2.8 | 0.0 | 86.1 | 7.8 |
| | 550 | 5 | 36.6 | 5.1 | 9.7 | 8.4 | 47.9 | 14.8 | 12.4 | 0.7 | 0.8 | 78.6 | 14.3 |
| | 600 | 5 | 67.7 | 7.3 | 13.5 | 6.9 | 48.0 | 12.2 | 10.4 | 0.4 | 1.4 | 61.4 | 21.4 |

(Evaluation 2)

In Evaluation 1, the reaction temperature was fixed at 600° C., and the reaction products were introduced into the gas chromatography after five minutes elapsed from the beginning of the reaction, after 55 minutes elapsed, after 105 minutes elapsed, and after 155 minutes elapsed, the reaction products were separated by using a capillary column, and the properties and quantities of the respective products and unreacted substances were measured by using a flame ionization detector (FID). Except the above, Evaluation 2 was carried out in the same manner as in Evaluation 1. In addition, the time dependency of the inversion rate was obtained. The results are shown in FIG. 8.

Figure 7:
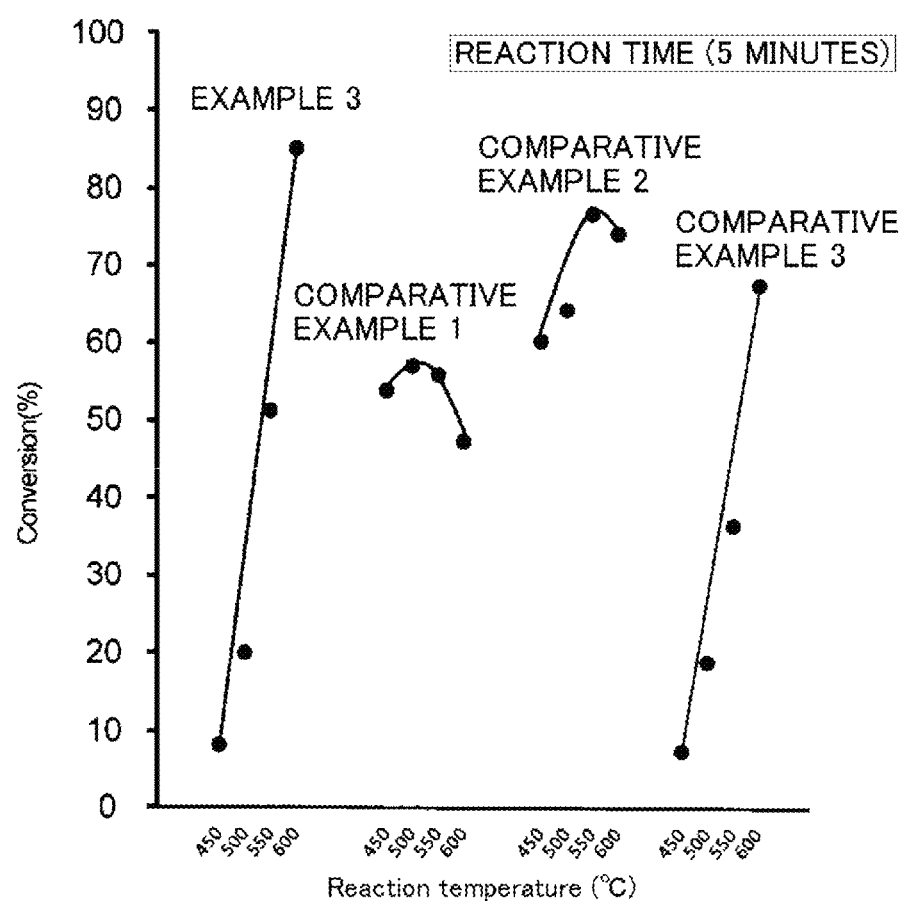
FIG. 7 is a graph showing the temperature dependency of the inversion rate when cracking of hexane is carried out using beta-type zeolites obtained in examples and comparative examples as catalysts.
Figure 8:
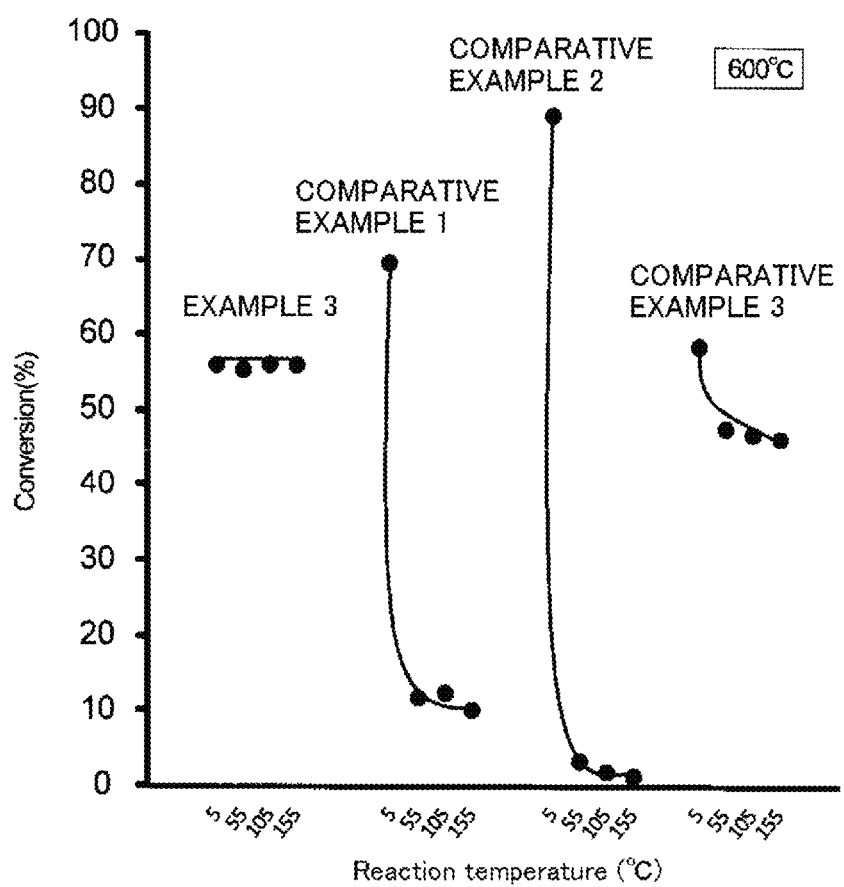
FIG. 8 is a graph showing the time dependency of the inversion rate when cracking of hexane is carried out using beta-type zeolites obtained in the examples and the comparative examples as catalysts.

As is evident from the results shown in Table 5 and FIGS. 7 and 8, it is found that, when the beta-type zeolite obtained in Examples 6 to 18

Figure 9:
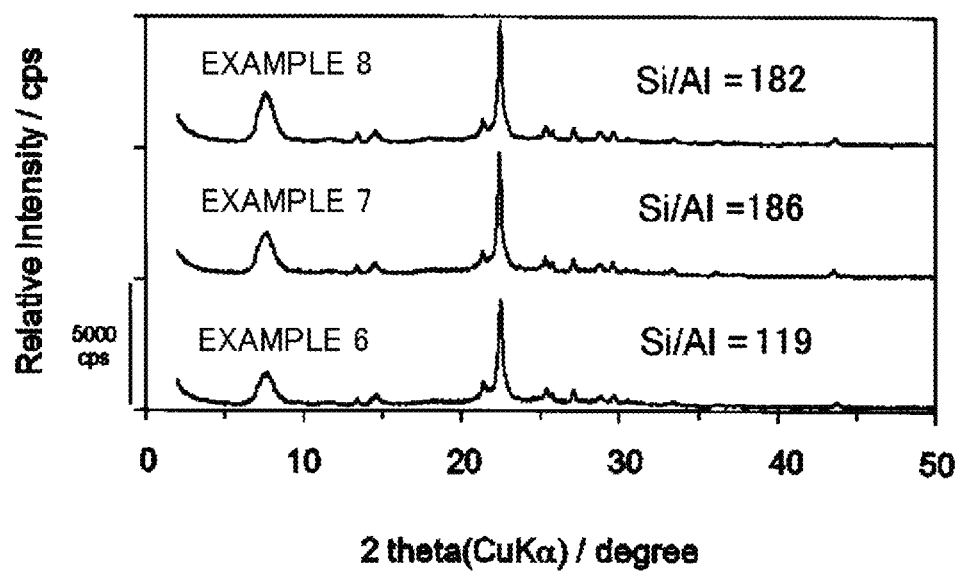
FIG. 9 shows X-ray diffraction diagrams of beta-type zeolites obtained in Examples 6 to 8.
Figure 10:
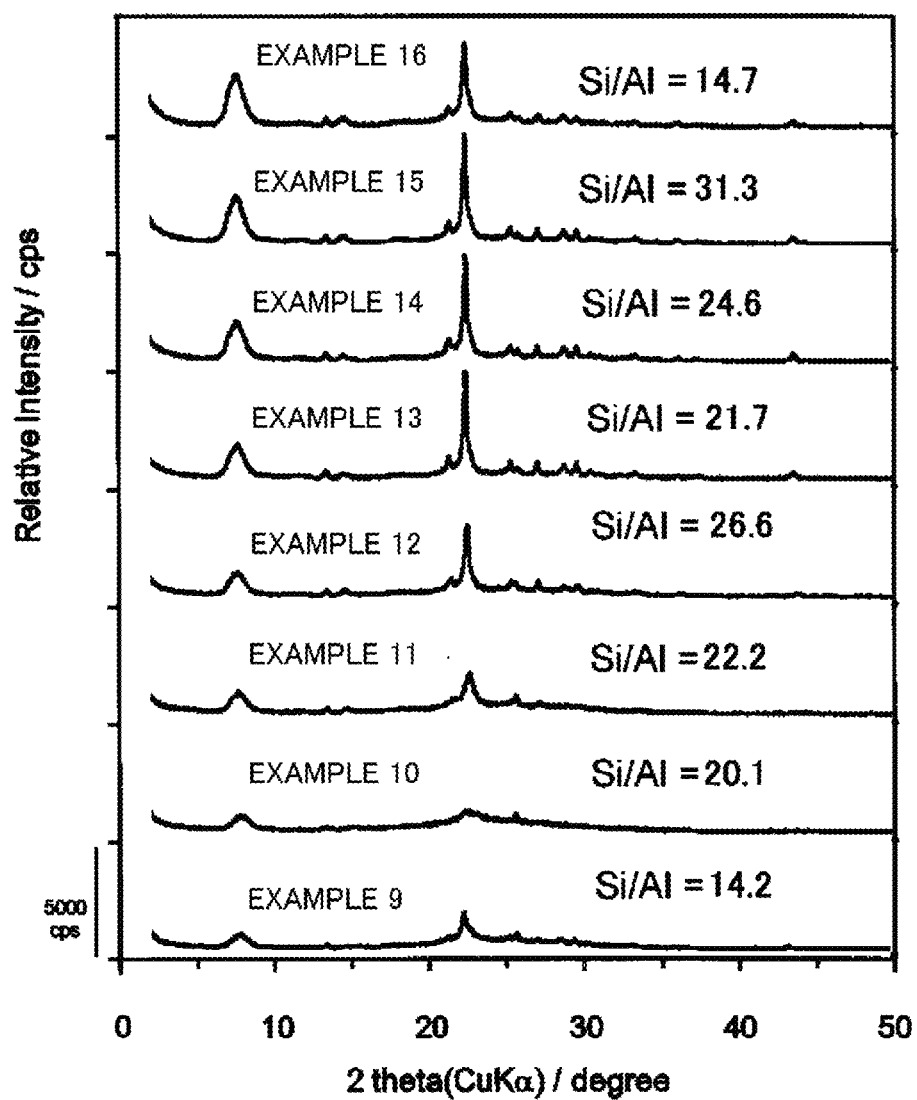
FIG. 10 shows X-ray diffraction diagrams of beta-type zeolites obtained in Examples 9 to 16.
Figure 11:
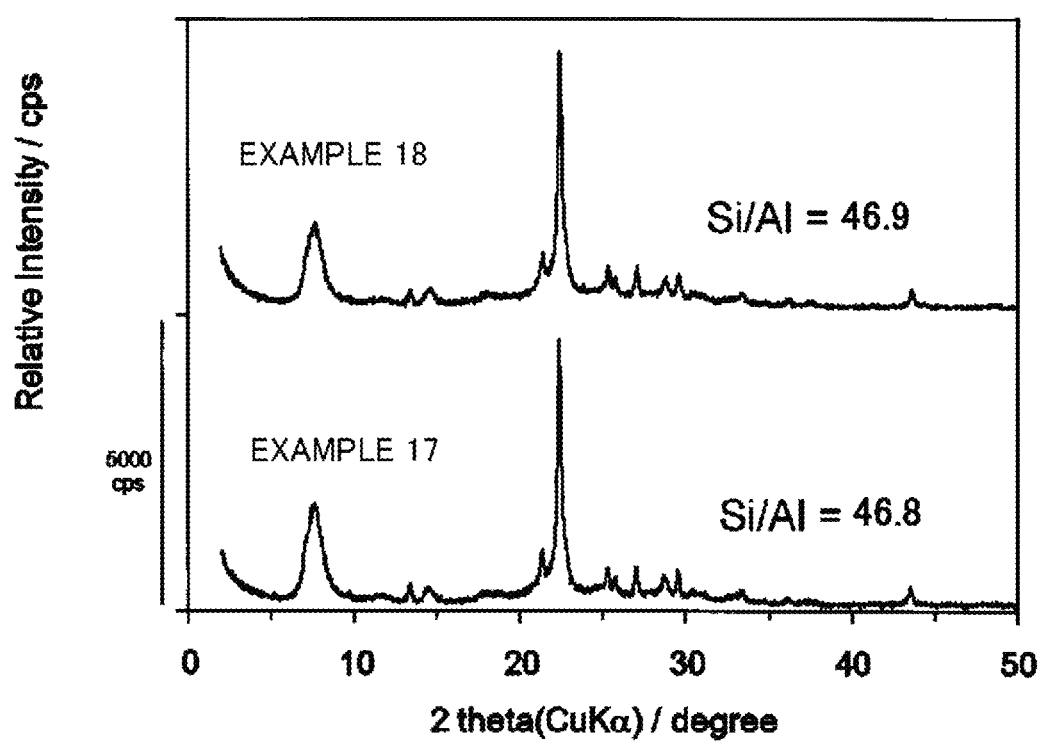
FIG. 11 shows X-ray diffraction diagrams of beta-type zeolites obtained in Examples 17 and 18.

Beta-type zeolites were obtained in the same manner as in Example 1 except that the manufacturing conditions described in Table 6 below were employed. The X-ray diffraction diagrams of the beta-type zeolites obtained in Examples 6 to 8 are shown in FIG. 9. The X-ray diffraction diagrams of the beta-type zeolites obtained in Examples 9 to 16 are shown in FIG. 10. The X-ray diffraction diagrams of the beta-type zeolites obtained in Examples 17 and 18 are shown in FIG. 11. In addition, the Si/Al ratios obtained from element analyses were described in the drawings. Meanwhile, while not shown, the beta-type zeolites obtained in Examples 6 to 18 had a substantially octahedral shape. Table 6 below also describes the manufacturing conditions employed in Examples 1 to 5.

TABLE 6

| | Conditions of the water vapor exposure process | | Conditions of the acid treatment process | | |
| --- | --- | --- | --- | --- | --- |
| | Temperature (° C.) | Exposure time (h) | Concentration (mol/L) | Temperature (° C.) | Time (h) |
| Example 1 | 700 | 24 | 0.1 | 80 | 2 |
| Example 2 | | | 0.5 | | |
| Example 3 | | | 1.0 | | |
| Example 4 | | | 2.0 | | |
| Example 5 | | | 8.0 | | |
| Example 6 | | | 8.0 | 130 (*) | 2 |
| Example 7 | | | 8.0 | | 24 |
| Example 8 | | | 13.4 | | |
| Example 9 | 150 | | 0.1 | 80 | 2 |
| Example 10 | 250 | | | | |

TABLE 6-continued

| | Conditions of the water vapor exposure process | | Conditions of the acid treatment process | | |
|---|---|---|---|---|---|
| | Temperature (° C.) | Exposure time (h) | Concentration (mol/L) | Temperature (° C.) | Time (h) |
| Example 11 | 350 | | | | |
| Example 12 | 450 | | | | |
| Example 13 | 550 | | | | |
| Example 14 | 650 | | | | |
| Example 15 | 750 | | | | |
| Example 16 | 850 | | | | |
| Example 17 | 700 | 2 | 0.1 | | |
| Example 18 | | 6 | | | |

(*) In Examples 6 to 8, the acid treatment is carried out by refluxing an acid in an oil bath at 130° C., and "130° C." described herein refers to the temperature of the oil bath.

From the results in the X-ray diffraction diagrams of Examples 1 to 8 shown in FIGS. 3 and 9, it is found that, when the concentration of the acid is increased, or the time of the acid treatment is extended in the acid treatment process, the Si/Al ratio of the beta-type zeolite increases. On the other hand, it is found that, even when the concentration of the acid is increased up to 13.4 mol/L, and the time of the acid treatment is extended up to 24 hours, the breaking of the crystal structure of the beta-type zeolite does not occur. In addition, from the results in the X-ray diffraction diagrams of Examples 9 to 16 in FIG. 10, it is found that, particularly, in the water vapor exposure process, in a case in which the temperature of the water vapor is 550° C. to 750° C. (Examples 13 to 15), more of the crystal structure of the beta-type zeolite is maintained compared to a case in which the temperature of the water vapor is 150° C. to 450° C., which is a lower temperature than the above temperature (Examples 9 to 12). In addition, from the results in the X-ray diffraction diagrams of Examples 3, 17 and 18 shown in FIGS. 3 and 11, it is found that, in a case in which the time of the water vapor exposure is shortened to 2 hours (Example 17) or 6 hours (Example 18) from 24 hours (Example 3), the Si/Al ratio of the beta-type zeolite decreases, but there is no change in the crystallinity.

Example 19

(1) Synthesis of a Seed Crystal

N,N,N',N'-tetraethylbicyclo[2.2.2]-oct-7-ene-2,3:5,6-dipyrrolidinium diiodide was used as the organic SDA. According to the description in the specification of U.S. Pat. No. 6,049,018, a reaction mixture was prepared using aluminum hydroxide as the alumina source, colloidal silica as the silica source, and potassium hydroxide as the alkali source, and was heated at 160° C. for 16 days using a static method. A MSE-type zeolite obtained by heating and firing the product in the air at 540° C. for 8 hours was used as the seed crystal. The Si/Al ratio was 12.0. The crystal of the MSE-type zeolite not including an organic substance was used as the seed crystal.

(2) Synthesis of the OSDA-Free MSE-Type Zeolite

Sodium aluminate (0.096 g) and 36% sodium hydroxide (2.147 g) were dissolved in pure water (10.74 g), thereby producing an aqueous solution. A mixture of fine powder-form silica (Cab-O-sil, M-5, 2.022 g) and the seed crystal (0.202 g) was added to the aqueous solution little by little, stirred and mixed, thereby producing a reaction mixture. In the reaction mixture, the $SiO_2/Al_2O_3$ ratio was 100, the $(Na_2O+K_2O)/SiO_2$ ratio was 0.3, the $K_2O/(Na_2O+K_2O)$ ratio was 0, and the $H_2O/SiO_2$ ratio was 20. A mixture of this reaction mixture and the seed crystal was put into a 60 cc stainless steel closed vessel, and statically heated at 140° C. for 60 hours under an autogenous pressure without aging and stirring. After the closed vessel was cooled, the product was filtered and washed with warm water, thereby producing white powder. As a result of carrying out an X-ray diffraction measurement on this product, it was confirmed that the product was a MSE-type zeolite. As a result of a composition analysis, the Si/Al ratio was 6.8.

(3) Ion Exchange Treatment

The obtained OSDA-free MSE-type zeolite was used as the raw material, and was dispersed in an aqueous solution of ammonium nitrate. The mass ratio of the OSDA-free beta-type zeolite, ammonium nitrate, and water was set to 1:2:50. This dispersion liquid was statically placed over 24 hours in a state of being heated at 80° C., thereby carrying out ion exchange. After that, filtration was carried out so as to separate the beta-type zeolite. After the operation of ion exchange and filtration was repeated one more time, the resultant was washed with water, and dried at 80° C., thereby producing an ammonium-type MSE-type zeolite.

(4) Exposure Using Water Vapor

The ammonium-type MSE-type zeolite was filled into the apparatus shown in FIG. 1. The filling amount was set to 1 g. A gas mixture of argon and water vapor was continuously circulated for 24 hours in a state in which the ammonium-type MSE-type zeolite was heated at 700° C. by the heating means 15 shown in the same drawing. The partial pressure of the water vapor was set to 12.2 kPa. The exposure using water vapor transformed the MSE-type zeolite from the ammonium-type into a proton-type.

(5) Acid Treatment

Figure 12:
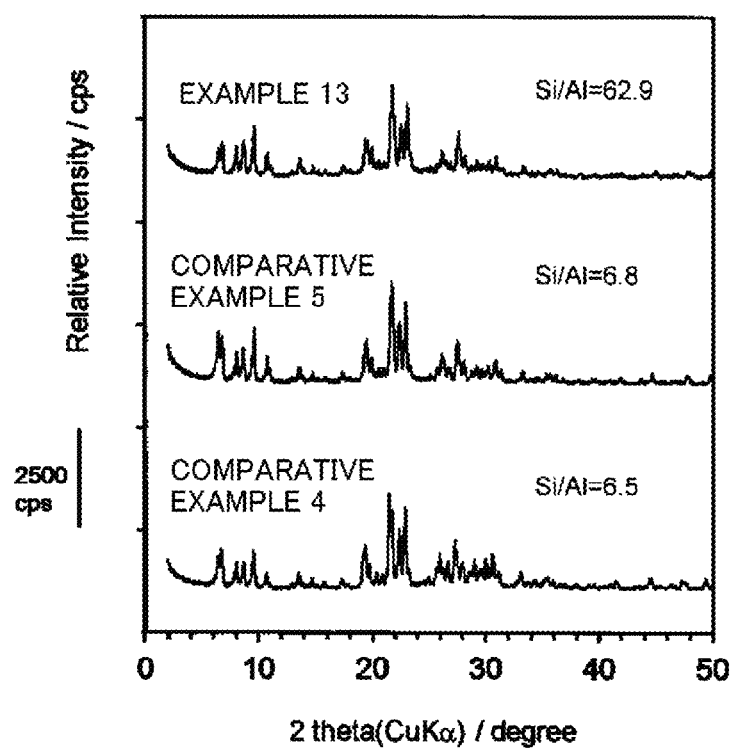
FIG. 12 shows X-ray diffraction diagrams of MSE-type zeolites obtained in Example 19 and Comparative examples 4 and 5.

The water vapor-exposed beta-type zeolite was subjected to an acid treatment using a 6.0 mol/L aqueous solution of nitric acid. The temperature of the aqueous solution of nitric acid was set to 80° C. The aqueous solution of nitric acid (10 mL) was added to the MSE-zeolite (0.1 g). The treatment was carried out for 2 hours while stirring the solution using a magnetic stirrer. In the above manner, a target MSE-type zeolite was obtained. The X-ray diffraction diagram of the obtained beta-type zeolite is shown in FIG. 12. The Si/Al ratio obtained from an element analysis was 62.9.

Comparative Example 4

A proton-type MSE-type zeolite was obtained by carrying out a direct thermal treatment without carrying out the exposure using water vapor and the acid treatment after ion-exchanging the OSDA-free MSE-type zeolite in Example 19. The conditions of the thermal treatment were set to a temperature of 650° C., a time of 60 minutes, and an air circulation amount of 40 cm$^3$/min. The X-ray diffraction diagram of the obtained MSE-type zeolite is shown in FIG. 12. In addition, the Si/Al ratio obtained from an element analysis was 6.5.

Comparative Example 5

A proton-type MSE-type zeolite was obtained by carrying out a direct thermal treatment without carrying out the acid treatment after ion-exchanging the OSDA-free MSE-type zeolite, and then exposing the zeolite using water vapor in Example 19. The conditions of the thermal treatment were set to a temperature of 650° C., a time of 60 minutes, and an air circulation amount of 40 cm$^3$/min. The X-ray diffraction diagram of the obtained MSE-type zeolite is shown in FIG. 12. In addition, the Si/Al ratio obtained from an element analysis was 6.8.

(Evaluation)

Figure 13:
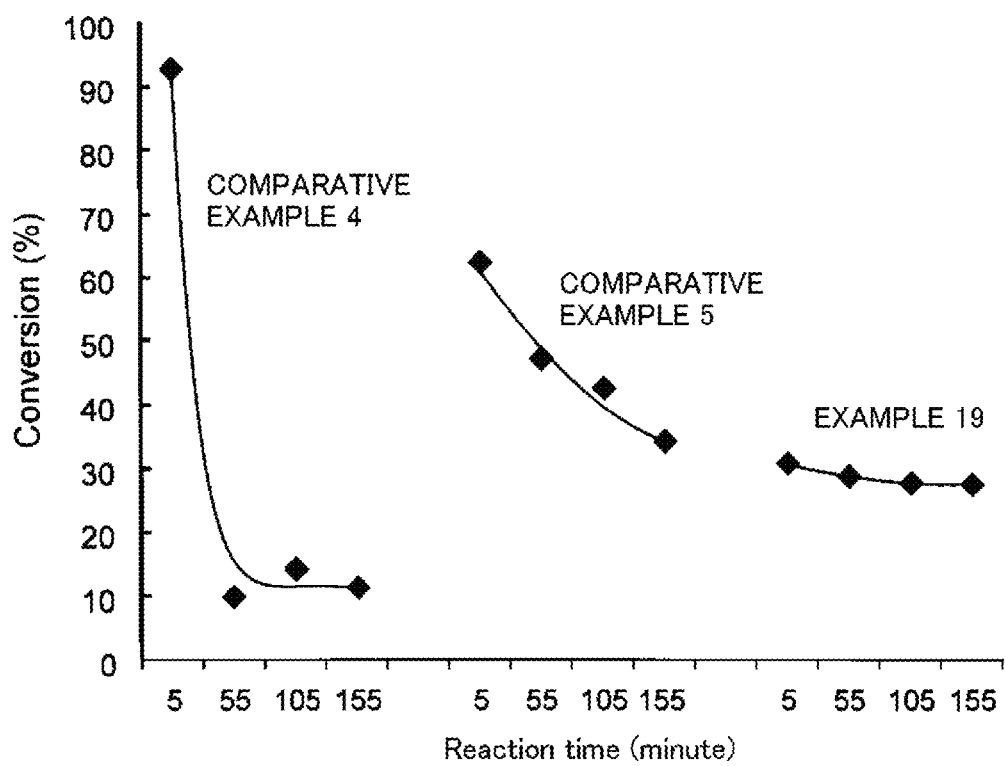
FIG. 13 is a graph showing the time dependency of the inversion rate when cracking of hexane is carried out using MSE-type zeolites obtained in the examples and the comparative examples as catalysts.

For the MSE-type zeolites obtained in Example 19 and Comparative examples 4 and 5, evaluation of the catalytic activity during the cracking reaction of hexane was carried out according to Evaluation 2 described above. The time dependency of the inversion rate is shown in FIG. 13. In addition, the selection rates into the respective products and the yield of propylene are shown in Table 7.

zeolite is not observed. In contrast to the above, in the MSE-type zeolite of Comparative example 4, in which only the ion exchange treatment was carried out, and the MSE-type zeolite of Comparative example 5, in which only the ion exchange treatment and the water vapor exposure process were carried out, and the acid treatment was not carried out, the yields of propylene was low, and deactivation was observed.

EXPLANATION OF REFERENCE

10 WATER VAPOR EXPOSURE APPARATUS
11 HOLDING TUBE
12 WATER VAPOR SUPPLY SOURCE
13 INERT GAS SUPPLY SOURCE
14 WATER
15 HEATING MEANS

The invention claimed is:

1. A beta-type zeolite which has a substantially octahedral shape, has a Si/Al ratio of 14 or more, and is a proton-type zeolite.

2. The beta-type zeolite according to claim 1, wherein the Si/Al ratio is 40 or more.

3. The beta-type zeolite according to claim 1 obtained by transforming a raw material beta-type zeolite synthesized without using a structure directing agent into an ammonium-type zeolite through ion exchange, then, exposing the beta-type zeolite to water vapor, and subjecting the exposed beta-type zeolite to an acid treatment.

4. A catalytic cracking catalyst of paraffin including the beta-type zeolite according to claim 1.

5. A manufacturing method of a beta-type zeolite which has a substantially octahedral shape in which a raw material beta-type zeolite is transformed into an ammonium-type zeolite through ion exchange, then, exposed to water vapor, and

TABLE 7

| Catalyst | Temperature (° C.) | TOS (min) | Inversion rate (%) | $C_1$ | $C_2=$ | $C_2$ | $C_3=$ | $C_3$ | $C_4=$ | $C_4$ | $C_5=$ | $C_5$ | Aromatic | $C_3=$ yield (C %) |
|---|---|---|---|---|---|---|---|---|---|---|---|---|---|---|
| Example 19 | 600 | 5 | 31.5 | 10.8 | 18.3 | 6.4 | 44.1 | 6.6 | 7.7 | 3.6 | 1.2 | 0.5 | 0.8 | 13.5 |
|  |  | 55 | 29.5 | 10.7 | 17.6 | 5.9 | 45.7 | 6.8 | 7.4 | 3.6 | 1.2 | 0.4 | 0.7 | 15.1 |
|  |  | 105 | 28.3 | 10.8 | 17.6 | 5.9 | 45.5 | 7.0 | 7.4 | 3.6 | 1.3 | 0.4 | 0.7 | 14.7 |
|  |  | 155 | 28.2 | 10.8 | 17.8 | 6.0 | 45.2 | 7.0 | 7.4 | 3.5 | 1.4 | 0.4 | 0.6 | 13.6 |
| Comparative example 4 | 600 | 5 | 92.8 | 17.5 | 27.3 | 6.5 | 26.8 | 10.6 | 2.9 | 1.5 | 0.0 | 0.1 | 6.9 | 19.8 |
|  |  | 55 | 9.9 | 21.7 | 36.3 | 4.7 | 22.8 | 1.4 | 10.4 | 0.4 | 1.4 | 0.9 | 0.0 | 2.2 |
|  |  | 105 | 14.7 | 21.5 | 39.2 | 3.7 | 22.8 | 1.3 | 9.5 | 0.0 | 1.0 | 1.0 | 0.0 | 1.9 |
|  |  | 155 | 12.0 | 21.8 | 37.2 | 4.7 | 22.3 | 1.2 | 10.2 | 0.3 | 1.3 | 1.0 | 0.0 | 2.2 |
| Comparative example 5 | 600 | 5 | 62.9 | 11.7 | 22.2 | 5.3 | 38.0 | 4.9 | 10.4 | 2.0 | 0.3 | 0.3 | 5.0 | 21.7 |
|  |  | 55 | 47.9 | 11.6 | 22.9 | 5.2 | 36.7 | 4.6 | 11.2 | 2.0 | 0.4 | 0.4 | 5.1 | 15.7 |
|  |  | 105 | 43.2 | 12.6 | 23.2 | 5.1 | 35.8 | 4.1 | 12.0 | 1.9 | 0.6 | 0.5 | 4.3 | 11.9 |
|  |  | 155 | 35.0 | 13.8 | 23.6 | 4.9 | 33.8 | 3.6 | 12.9 | 1.7 | 0.8 | 0.6 | 4.3 | 8.1 |

As is evident from the results shown in FIG. 13 and Table 7, it is found that, when the MSE-type zeolite obtained in Example 19 is used as a catalyst, and cracking of hexane is carried out, $C_3=$(propylene), which is a useful substance as a chemical raw material, is generated at a high yield. In addition, it is also found that the deactivation of the MSE-type subjected to an acid treatment, thereby obtaining the beta-type zeolite having a substantially octahedral shape and having an increased Si/Al ratio of 14 or more, wherein a beta-type zeolite synthesized without using a structure directing agent is used as the raw material beta-type zeolite to be ion-exchanged.

6. The manufacturing method according to claim 5, wherein the ion-exchanged raw material beta-type zeolite is exposed to water vapor at 150° C. to 1000° C. for 1 hour to 48 hours.

7. The manufacturing method according to claim 5, wherein the raw material beta-type zeolite which has been exposed to water vapor is subjected to an acid treatment at 40° C. to 100° C. for 1 hour to 24 hours using a mineral acid.

8. The manufacturing method according to claim 5, wherein a beta-type zeolite having a Si/Al ratio of 40 or more is obtained.

\* \* \* \* \*